United States Patent
Brown et al.

(10) Patent No.: US 11,871,975 B2
(45) Date of Patent: Jan. 16, 2024

(54) SMART SURGICAL SCREWDRIVER

(71) Applicant: Wake Forest University Health Sciences, Winston-Salem, NC (US)

(72) Inventors: Philip J. Brown, Winston-Salem, NC (US); Andrea Morgan Rich, Winston-Salem, NC (US); Aaron Ross Van Gorkom, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 16/339,400

(22) PCT Filed: Oct. 5, 2017

(86) PCT No.: PCT/US2017/055276
§ 371 (c)(1),
(2) Date: Apr. 4, 2019

(87) PCT Pub. No.: WO2018/067784
PCT Pub. Date: Apr. 12, 2018

(65) Prior Publication Data
US 2020/0038084 A1 Feb. 6, 2020

Related U.S. Application Data

(60) Provisional application No. 62/404,579, filed on Oct. 5, 2016.

(51) Int. Cl.
*A61B 17/16* (2006.01)
*A61B 17/88* (2006.01)

(52) U.S. Cl.
CPC ...... *A61B 17/8875* (2013.01); *A61B 17/1626* (2013.01); *A61B 2560/0462* (2013.01); *A61B 2560/0475* (2013.01)

(58) Field of Classification Search
CPC ............ A61B 17/1624; A61B 17/1626; A61B 17/1628; A61B 17/8875–8894; A61B 2090/067
USPC ........................................................ 606/104
See application file for complete search history.

(56) References Cited

U.S. PATENT DOCUMENTS

| | | |
|---|---|---|
| 5,303,601 A | 4/1994 | Schönberger et al. |
| 5,476,014 A | 12/1995 | Lampe et al. |
| 5,538,423 A | 7/1996 | Coss et al. |
| 6,458,142 B1 | 10/2002 | Faller et al. |

(Continued)

FOREIGN PATENT DOCUMENTS

| | | |
|---|---|---|
| CA | 2275426 A1 | 7/1998 |
| WO | 2018067784 | 4/2018 |

OTHER PUBLICATIONS

Kulkarni, Sanjeev. https://www.princeton.edu/~cuff/ele201/kulkarni_text/human.pdf. p. 7 (1999-2001).*

(Continued)

*Primary Examiner* — Matthew J Lawson
(74) *Attorney, Agent, or Firm* — Kilpatrick Townsend & Stockton LLP

(57) ABSTRACT

Disclosed herein are surgical tool systems and methods of using such to install a fixator in a biological tissue. The systems are capable of accurately measuring torque and rotational velocity and providing real time feedback to a user during surgery.

18 Claims, 6 Drawing Sheets

(56) References Cited

U.S. PATENT DOCUMENTS

| | | |
|---|---|---|
| 9,241,693 B2 | 1/2016 | Taylor et al. |
| 2005/0116673 A1* | 6/2005 | Carl .................. A61B 17/1626 |
| | | 318/432 |
| 2005/0131415 A1 | 6/2005 | Hearn et al. |
| 2007/0151390 A1 | 7/2007 | Blumenkranz et al. |
| 2010/0057136 A1 | 3/2010 | Heiges et al. |
| 2014/0222012 A1 | 8/2014 | Belkoff et al. |
| 2015/0351819 A1* | 12/2015 | Gustafson .......... A61B 17/8875 |
| | | 606/104 |

OTHER PUBLICATIONS

PCT US Search Report and Written Opinion dated Jan. 2, 2018 for PCT Appl. No. PCT/US2017/055276.

PCT/US2017/055276, "International Preliminary Report on Patentability", dated Apr. 18, 2019, 7 pages.

\* cited by examiner

SMART SURGICAL SCREWDRIVER

CROSS-REFERENCE TO RELATED APPLICATIONS

This application is a 371 National Entry of PCT/US2017/055276, filed on Oct. 5, 2017, which claims priority to U.S. Provisional Patent Application No. 62/404,579 entitled "SMART SURGICAL SCREW DRIVER," filed Oct. 5, 2016, the entirety of which are hereby incorporated by reference.

This invention was made with government support under W81XWH-10-2-0165 awarded by the Medical Research and Development Command. The government has certain rights in the invention.

FIELD OF INVENTION

The present invention relates generally to surgical instruments.

BACKGROUND

The human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue or correct the deformity, which can require the use of fixators such as screws, nails. However, post-operative loosening of surgical screws, a condition that affects between 0.5% and 27% of patients, can ultimately lead to failure that requires further surgical intervention. Many studies have been conducted to better understand properties that influence screw pullout strength, or the force required to loosen a screw. These studies and even available related medical products are based on the concept that peak screw insertional torque of screws is a good indicator of successful and unsuccessful screw installation. This is somewhat debatable, as several studies have shown the correlation is not strong enough. Thus there is a need for a surgical tool system that takes torque and energy measurements during surgery and provides real-time feedback to clinicians to ensure the best screw fixation and surgical outcome for patients.

SUMMARY OF THE INVENTION

Disclosed herein is a surgical tool system comprising a surgical tool configured to install a fixator in a biological tissue; a first sensor, a second sensor, and a third sensor in communication with the surgical tool, wherein the first sensor is configured to obtain torque measurements, and the second sensor configured to obtain one or more rotational acceleration measurements during the installation, i.e., tapping and/or insertion of a fixator, and a third sensor is to receive time measurements. The surgical tool system further comprises a microcontroller configured to receive measurements from the first and second, third sensors and calculate one or more torque parameters and one or more one energy-rotation parameter, generate one or more optimal ranges for the at least one torque parameter and at least one energy parameter. The surgical tool system disclosed herein further comprises a feedback mechanism configured to communicate a signal reflecting whether one or more torque parameter and one or more energy-rotation parameter are within or outside the one or more optimal ranges in real time.

In some embodiments, the system further comprises a power source. In some embodiments, the second sensor comprises a gyroscope.

In some embodiments, the microcontroller further comprises a means to adjust the tool such that the one or more torque parameter and one or more energy parameter are maintained substantially within the one or more optimal ranges. In some embodiments, the first, second, and third sensors are configured to obtain measurements at a frequency of at least 5, at least 20, at least 40, or at least 60 Hz. In some embodiments, the one or more optimal ranges are generated based one or more factors selected from age, gender, height, weight, BMI, race, and BMD.

In some embodiments, the feedback mechanism is a visual feedback mechanism or a tactile feedback mechanism. In some embodiments, wherein the one or more torque parameters are selected from peak torque and mean torque. In some embodiments, the one or more energy-rotation parameter comprise total insertional energy and energy density. In some embodiments, the fixator is a pedicle screw or cortical screw. In some embodiments, the system further comprises a Bluetooth module for data transmission and storage.

Also provided herein is a method for installing a fixator in a biological tissue, the method comprising: loading an external fixator to a surgical tool, operating the surgical tool to start installing the fixator in the biological tissue, measuring one or more torque measurements, one or more rotational acceleration measurements, and one or more time measurements, calculating one or more torque parameters, one or more energy-rotation parameters, communicating to a user a signal reflecting whether the values of the one or more torque parameter and the one or more energy parameter fall outside one or more optimal ranges, and adjusting the operation of the tool such that values of the one or more torque parameters and one or more energy-rotation parameters are within the one or more optimal ranges, if the values are outside the optimal ranges, and repeating steps above from measuring to adjusting until the installation is complete.

In some embodiments, the method comprises, before the step (a) of the method above, i) tapping with the surgical tool in the location of the biological tissue where a fixator is to be installed, ii) measuring one or more torque measurements and one or more rotational velocity measurements during the tapping, iii) calculating at least one torque parameter and at least one energy-rotation parameter during the tapping, and iv) adjusting tap size if values of the one or more torque measurements and/or one or more energy-rotation parameter calculated insertional energy fall outside optimal ranges, or continuing with tapping and installing the fixator if the one or more torque measurements and one or more energy parameter calculated insertional energy fall within optimal ranges.

In some embodiments, the measurements are performed at a frequency of at least 10, at least 12, at least 15, at least 20, or at least 30 times per second. In some embodiments, the signal is a visual signal or a tactile signal. In some embodiments, the fixator is a pedicle screw or a cortical screw. In some embodiments, the method further comprises transmitting data from the tool via a Bluetooth module.

BRIEF DESCRIPTION OF THE DRAWINGS

The present application includes the following figures. The figures are intended to illustrate certain embodiments and/or features of the invention, and to supplement any description(s) of the invention. The figures do not limit the scope of the invention, unless the written description expressly indicates that such is the case.

DETAILED DESCRIPTION

Figure 1:
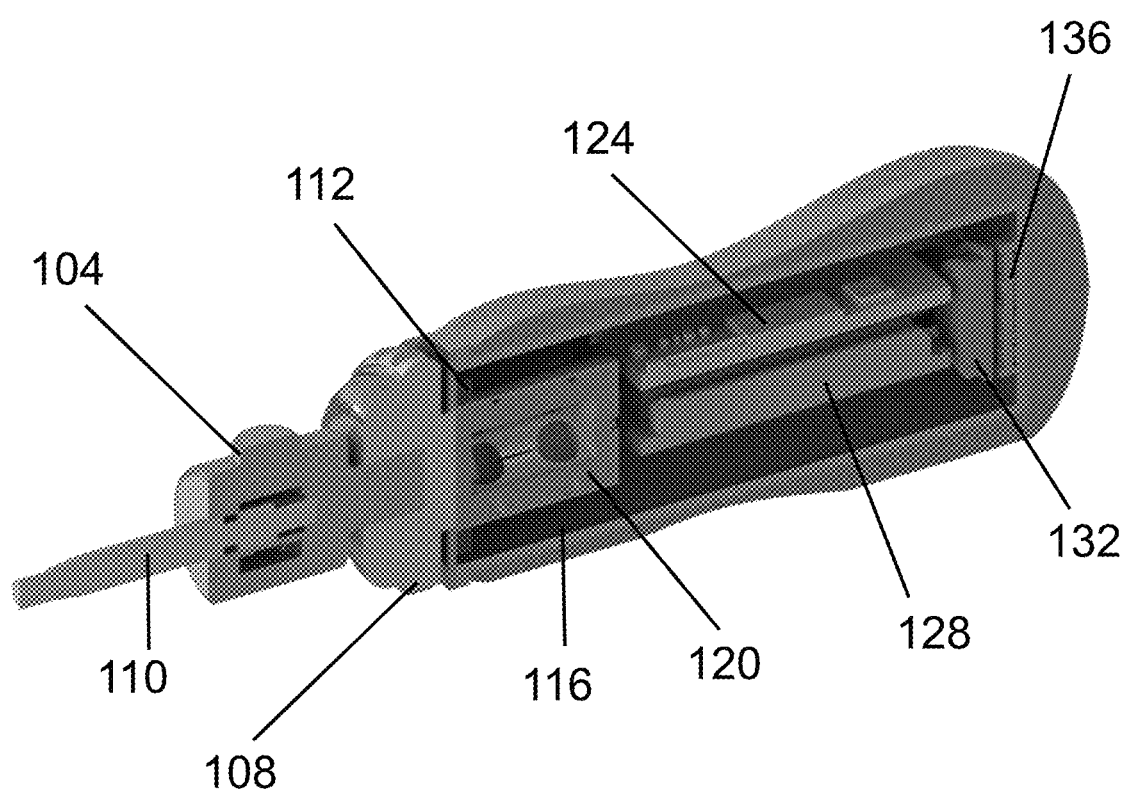
FIG. 1 is an illustration showing an angled cross-sectional view of one embodiment of a smart driver surgical tool system.

The following description recites various aspects and embodiments of the present invention. No particular embodiment is intended to define the scope of the invention. Rather, the embodiments merely provide non-limiting examples various methods and systems that are at least included within the scope of the invention. The description is to be read from the perspective of one of ordinary skill in the art; therefore, information well known to the skilled artisan is not necessarily included.

1. Definitions

The following terms, unless otherwise indicated, shall be understood to have the following meanings:

As used herein, the terms "a," "an," and "the" can refer to one or more unless specifically noted otherwise.

Throughout this application, the term "about" is used to indicate that a value includes the inherent variation of error for the device, the method being employed to determine the value, or the variation that exists among the study subjects.

As used herein, the terms "user," "surgeon," and "operator" are used interchangeably to refer to a person who operates the surgical tool system.

As used herein, the term "pedicle screw" is used to refer to a type of bone screw designed for implantation into a vertebral pedicle. The term "cortical screw" is used to refer to a type of bone screws designed for implantation into cortical bone tissue. These screws are used to correct deformity, and/or treat trauma. Similar to other bone screws, pedicle screws and cortical screws may be used in instrumentation procedures to affix rods and plates to the spine. The screws may also be used to immobilize part of the spine to assist fusion by holding bony structures together. Typical screws are made of Titanium, which is highly resistant to corrosion and fatigue, and is magnetic resonance imaging ("MRI")-compatible.

As used herein, the term "real time" is used to refer to the instantaneous communication of measurements from the sensors and values calculated from the measurements, such as the torque measurements and rotational velocity, to the user during tapping or fixator insertion procedures. The system disclosed herein is able to provide real time communication to a user because the sensors take measurements, transmit values, and provide feedback at a very high frequency to the microcontroller, which then provides the feedback to the user.

As used herein, the term "tap size" is used to refer to the incremental diameter of the thread cutting tool in preparation for fixator installation into the boney structure As used herein the term "torque" is used to refer to a measure of the turning force or moment on an object such as a bolt. The magnitude of torque depends on the force applied, the length of the lever arm connecting the axis to the point of force application, and the angle between the force vector and the lever arm.

As used herein, the term "mean torque" is used to refer to average turning force or moment during a measuring period. The term "peak torque" is used to refer to the maximum turning force during a measuring period.

As used herein, the term "insertional energy" is used to refer to total amount of energy or work applied during the tapping or fixator insertion procedure. The value of insertional energy is the time integral of the instantaneous torque and rotational velocity.

As used herein, the term "energy density" is used to refer to total amount of energy or work applied during the tapping or fixator insertion procedure divided by the total number of rotations or the linear distance covered during insertion of the tap or fixator.

As used herein, the term "mean power" is used to refer to the average rate of power during tapping or the fixator insertion procedure. The value of the mean power is the quotient of the value of insertional energy divided by the length of time.

As used herein, the term "parameter" is used to refer to any measured or computed variable reflecting the performance of the fixator installation. The values of the parameters are derived from the measurements from the sensors. A parameter disclosed herein may be relating to torque, rotation, time, energy, or any combination or derivative of the four including means, minimums, and maximums of each property. Torque parameters include instantaneous torque, mean torque, peak torque, time derived rates of torque. Energy parameters include insertional energy or work, energy density, power, time derived rates of energy or power. Rotational parameters include total rotations, rotational velocity, and rotational acceleration. The mean, maximum, minimum, or median values for any measured or calculated parameter may be incorporated into calculations to determine optimal ranges for a particular subject.

As used herein, the term "energy-rotation parameter" is used to refer to any parameter that is an energy parameter or a rotation parameter as described above.

As used herein, the term "optimal range" refers to a range of the values of a parameter or a combination of parameters, once reached during the installation procedure, can minimize loosening of a fixator from the biological tissue in which the fixator is installed.

2. Surgical Tool System

This invention provides a surgical tool system that monitors and optimizes the installation of a fixator to a biological tissue. In addition to the surgical tool, the system comprises two or more sensors and a microcontroller. The system further comprises a feedback mechanism that allows real time communication with a user regarding whether optimal insertional parameters are reached during screw insertion, thus reducing the likelihood of screw loosening.

a. Surgical Tool

The surgical tool of the system disclosed herein can perform tapping in the biological tissue in which the fixator is to be installed (see the section entitled "Methods"). The tool is also configured to engage a fixator such that the fixator remains in contact with the tool during the installation. A fixator is an external component that can be inserted into the biological tissue. A fixator is typically used for attachment of implants to bone, bone to bone fixation or for soft tissue fixation or anchorage. A fixator can be any material that is suitable for use inside a human body. For example, it can be metal, e.g., stainless steel or titanium, bio-absorbable or plastic. In preferred embodiments, the fixator is made of materials that are resistant to corrosion and compatible with MRI. In some embodiments, the fixator is a surgical screw. In some embodiments, the fixator is a pedicle screw. In some embodiments, the fixator is a cortical screw. The configuration and size of the screw can vary depending on the person's age, and anatomy, as well as the characteristics of the bone structure, for example, the bone mineral density (BMD). Biological tissues to which the fixator can be installed include, but are not limited to, bone, ligaments, cartilage, etc. In some embodiments, the biological tissue is bone in the lumbar, thoracic, or cervical spinal regions.

The surgical tool portion of the system comprises an end bit connector and an adaptor. The adaptor can be used to load a fixator, e.g., a screw. In some embodiments, the surgical tool of the system also comprises a ratcheting mechanism, which allows for unidirectional rotation while preventing movement in the opposite direction. The surgical tool may comprise an external sheath that encloses functional components within the tool, and may allow a user to comfortably grip the smart driver surgical tool system. The surgical tool may also comprise an inner housing compartment that holds other functional components, e.g., microcontroller, sensors, etc.

b. Sensors

Embodiments of the surgical tool system disclosed herein comprise at least a torque sensor. The torque sensor may be configured to obtain torque measurements during insertion of the fixator. The surgical tool system may also comprise a rotational accelerometer. The rotational accelerometer may be configured to obtain rotational measurements during the tapping and the insertion of the fixator. A torque sensor, also commonly referred to a torque cell, as disclosed herein, measures torque and converts the torque value into an electrical signal. A torque sensor typically comprises one or more strain gauges, which are bonded to a beam or structural member that deforms when a moment is applied. Deflection induces a strain that changes its resistance, which can be converted into a calibrated output signal using an electrical circuit.

The surgical tool system disclosed herein may further comprise at least one sensor that measures rotational acceleration during the operation of the system which is then later converted into rotational velocity and rotational displacement. These sensors are commonly referred to as rotational accelerometers. In some embodiments, the rotational accelerometer is a gyroscope that can fit inside the surgical tool system. In some embodiments, the gyroscope is a three-axis gyroscope. In some embodiments, the surgical tool system disclosed herein comprise two, three, four or more gyroscopes (or rotational accelerometers). In some embodiments the surgical tool system may contain six accelerometers, three linear and three rotational.

The surgical tool system disclosed herein further comprises at least a third sensor that measures time when the other torque measurements and rotational measurements are taken.

The sensors disclosed herein can take measurements at a very high frequency. In some embodiments, the sensors take measurements at least 2, at least 5, at least 6, at least 10, at least 12, at least 13, at least 14, at least 15, at least 20 times, at least 25, at least 30, at least 40 times per second. In some embodiments, the sensors take measurements between 5 and 60 hz. The sensors may transmit these measurements to the microcontroller, which may calculate values of parameters that reflect the performance of the operation, e.g., mean torque, peak torque, mean rotational velocity, insertional energy, and mean power.

In some embodiments, the sensors disclosed herein are in communication with a wireless transmitter, e.g., a Bluetooth module, to transmit measurements to a computer, or other data storage and analyzing device.

c. Microcontroller

Embodiments of the system disclosed herein may comprise a microcontroller, which can receive the measurements from the sensors. In some embodiments, the microcontroller comprises a unit that performs analog to digital conversion of the analog sensor signals. In some embodiments, the microcontroller comprises a unit that receives sensor data and calculates values of parameters that reflect the performance of the operation, e.g., mean torque, peak torque, mean rotational velocity, insertional energy, and mean power. In certain embodiments, the microcontroller produces values of at least one torque parameter and one energy-rotation parameter.

The microcontroller disclosed herein may be configured to calculate and store optimal ranges for each parameter. The optimal range of one parameter for tapping is often different from the optimal range of the same parameter for the fixator insertion procedure. In some embodiments, the optimal ranges for the parameters are based on existing parameter values gleaned from previous, successful fixator installations. In some embodiments, these data are obtained from the same patient or from patients having undergone fixator installation in similar tissue with similar type of fixators during tapping or fixator insertion procedure. In some embodiments, these data are derived from patients having similar age and BMD and of same gender, etc. In some embodiments, the data used to determine the optimal ranges are transmitted into the microcontroller via a wireless transmitting module, i.e., a Bluetooth. In some embodiments, these data are stored in the microcontroller of the system. In some embodiments, the optimal range for a parameter for the fixator insertion procedure is determined based on the combination of the parameter values obtained during tapping immediately preceding the fixator insertion and the existing data from previous, successful fixator installations.

In some embodiments, a derived parameter, property I, is calculated based on a mathematical equation that includes values collected from sensor data including torque, rotational acceleration, and time. For example, the mathematical equation used to produce property I includes coefficients for the parameters used in the equation. In some embodiments, the mathematical equation is a sum of weighted values of the at least one torque parameter and at least one energy-rotation parameter. In some embodiments, the parameters in the equation comprise insertional energy. Additionally and/or alternatively, the parameters may comprise peak torque, mean torque, and insertional energy. In this way, an optimal range for property I during tapping and an optimal range for property I during insertion of the fixator can be determined from patient demographic information and experimental correlation analysis between demographic information, tap and screw insertion sensor output, and screw failure analysis including toggle strength and pullout strength.

The microcontroller disclosed herein may be configured to compare the value of at least one torque parameter and one energy-rotation parameter, and all other required parameters derived therefrom, to optimal ranges to provide feedback to clinicians during the tapping and insertion of the fixator procedures. In some embodiments, the feedback mechanism is a visual feedback, e.g., an emission of a light from a screen on the system. In some embodiments, the feedback is a tactile feedback, e.g., a vibration of the tool system. In some embodiments, if one or more parameters, e.g., mean torque, falls outside the optimal range, the microcontroller may provide the feedback to the user. In some embodiments, the microcontroller provides such feedback when the one or more of the parameter measurements fall outside the optimal ranges. The microcontroller can be programmed such that the type or intensity of the signals, e.g., color of LED lights, of the feedback correspond to whether the real time measurements are approaching, within, leaving, or exceeding the optimal ranges.

In some embodiments, the microcontroller disclosed herein is configured to automatically adjust the insertion of the fixator into the tissue to maintain parameters within the optimal ranges.

d. Power Source

In certain embodiments, the surgical tool system comprises a power source. The surgical tool system can be powered by any electric power source. In some embodiments, the power source is a battery pack in the system. In some embodiments, the system comprises an RF (radio frequency) wireless charging coil which allows the system to be re-charged without removing the battery pack. In some embodiments, the power source is an external power source.

In some embodiments, the system can be switched on or off by operation of a switch or a push button. In some embodiments, the system is turned on automatically upon a user's contact with the system (e.g., picking up the surgical tool system). In some embodiments, lack of contact by a user for some period of time results in automatic shut down to turn the system off.

e. Wireless Transmitting Module

In some embodiments, the system disclosed herein provides a wireless transmitting module, e.g., a Bluetooth module, which may transfer data from the microcontroller and/or sensors to a computer and/or other data storage or analysis devices. Exemplary transmission protocols include, without limitation, ISM (b) and FSK modulation or spread spectrum modulation. The computer or data storage or analysis device may be operably coupled to or include a visual display. These data can be used for further analysis and performance tracking of the fixator installed and are also useful in determining optimal ranges for future installations of similar surgical fixators.

FIG. 1 shows an angled cross-sectional view of one embodiment of a smart driver surgical tool system. An end bit connector 104 may be configured to hold an adaptor 110, which allows loading of a fixator. Also depicted is a ratcheting mechanism 108 allows for unidirectional rotation. An LED indicator ring 112 can provide light signals to notify the user (e.g., surgeon) of the indication whether calculated values resulting from measurements being detected by sensors are outside of or within the optimal ranges. In the embodiment shown here, the light is visible to the user through the gap between the ratcheting mechanism and the compartment 116 that encloses many of the components of the smart driver surgical tool. Those components can include a torque sensing cell 120, a control circuit board (or microcontroller) 124 which includes a sensor for rotational velocity (or gyroscope), a battery pack 128, a vibration motor 132 which provides another means to notify a user whether the real time values resulting from the sensor measurements are outside or within the optimal ranges, and an RF (radio frequency) wireless charging coil 136 which allows the device to be re-charged without removing the battery pack.

Figure 2:
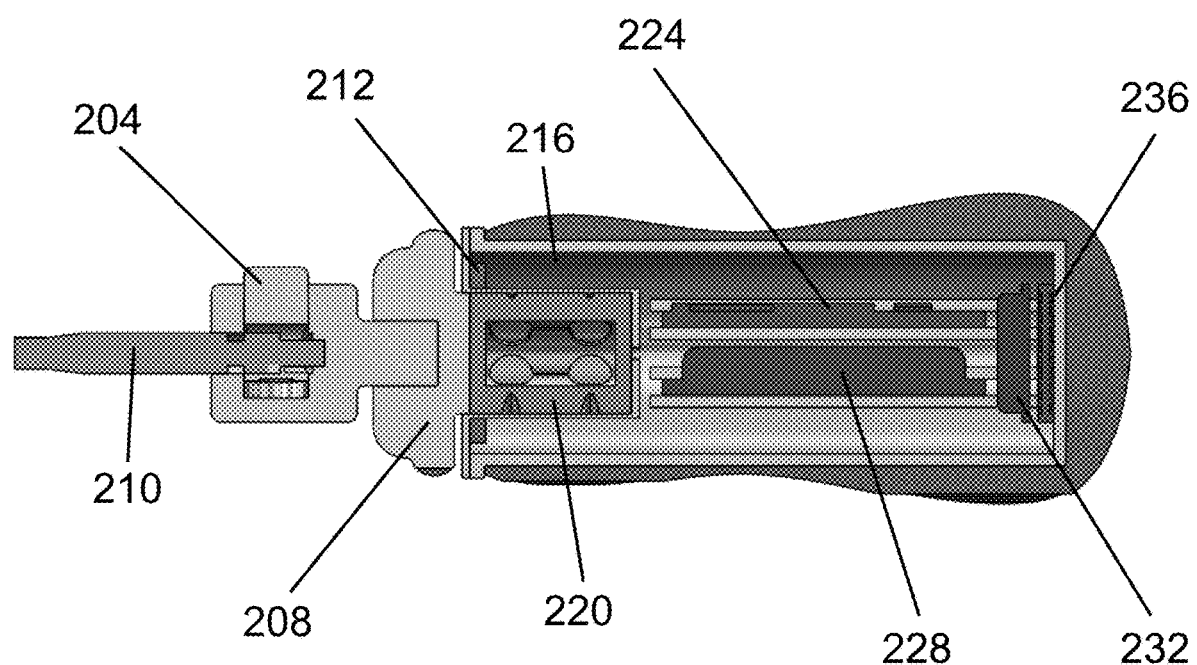
FIG. 2 is an illustration showing a direct cross-sectional side-view of the same embodiment of a surgical tool system as illustrated in FIG. 1.

FIG. 2 is an illustration showing a direct cross-sectional side-view of the same embodiment of a surgical tool system as illustrated in FIG. 1. Again, as shown in FIG. 1, an end bit connector 204 may be configured to hold an adaptor 210. A ratcheting mechanism 208 allows for unidirectional rotation. An LED indicator ring 212 can provide light signals to notify the user (e.g., surgeon) of the indication for calculated values resulting from measurements being detected by sensors. The light is visible to the user through the gap between the ratcheting mechanism and the compartment 216 that encloses many of the components of the smart driver surgical tool. Those components include a torque sensing cell 220, a control circuit board (or microcontroller) 224 which includes a sensor for rotational velocity (or gyroscope), a battery pack 228, a vibration motor 232, and an RF charging coil 236.

Figure 3:
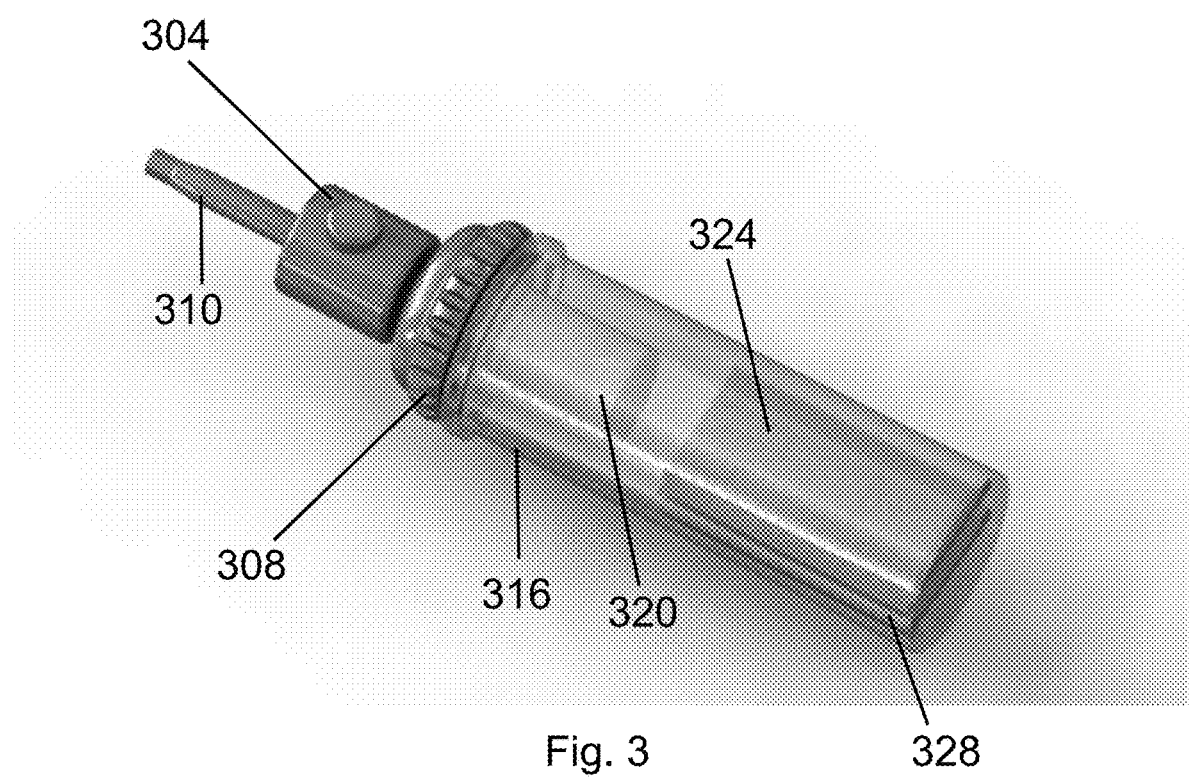
FIG. 3 is an illustration showing an external view of one embodiment of a device core of a surgical tool system (i.e., without the external components).

FIG. 3 is an illustration showing an external view of one embodiment of a device core of a surgical tool system (i.e., without the outermost components). Shown is an end bit connector 304 configured to hold an adaptor 310, which can be used to load a screw or other fixator. Again, a ratcheting mechanism 308 allows for unidirectional rotation. A compartment 316 (shown here as translucent such that components inside are visible) may enclose many of the components of the smart driver surgical tool system. Those components may include a torque sensing cell 320, a control circuit board (or microcontroller) 324 which includes a sensor for rotational velocity (or gyroscope), a battery pack 328. The embodiment depicted in FIG. 3 does not include a vibration motor or RF charging coil.

Figure 4:
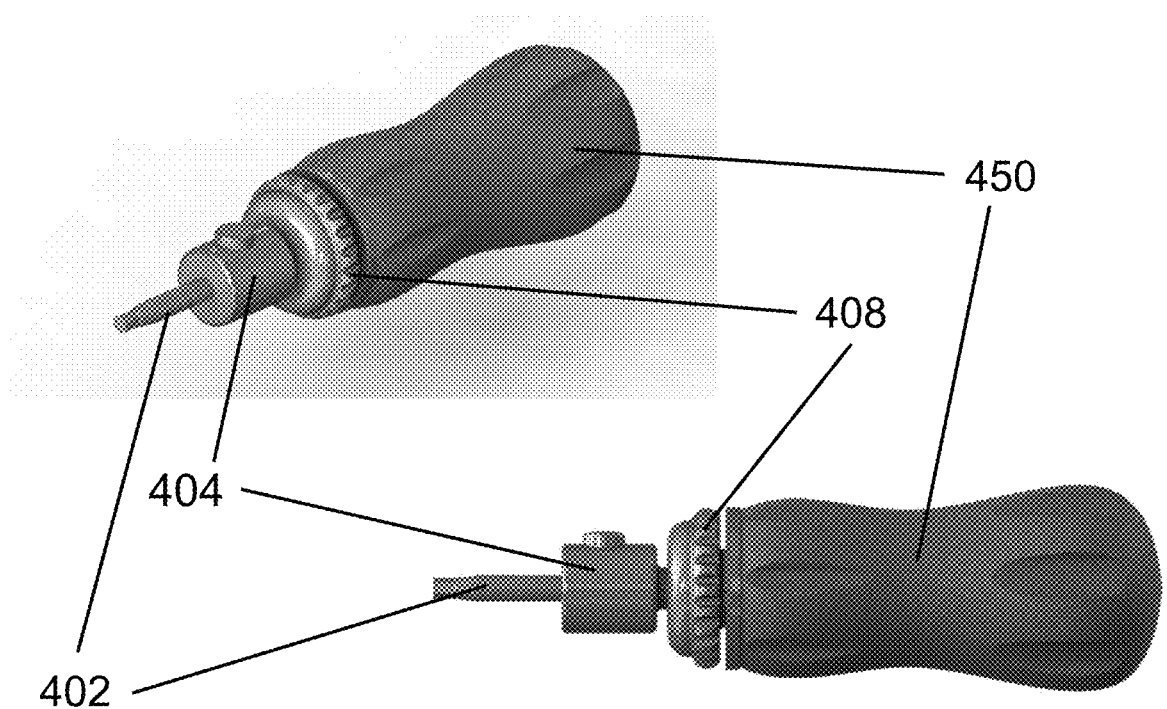
FIG. 4 is an illustration showing two external views of one embodiment of a smart driver a surgical tool system.

FIG. 4 is an illustration showing two external views of one embodiment of a smart driver a surgical tool system. The functional components in the device core are not visible here. An end bit connector 404 holds an adaptor 402, which can be used to engage a screw or other fixator. A ratcheting mechanism 408 allows for unidirectional rotation. An external sheath 450 encloses many functional components and may have a contoured or grooved surface to allow a user (e.g., surgeon) to comfortably grip the smart driver surgical tool system.

Figure 5:
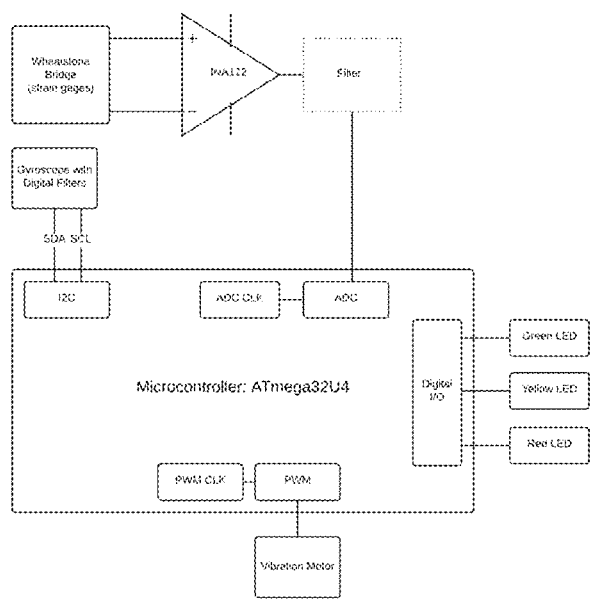
FIG. 5 is a block diagram showing the electronic components of the surgical tool system and how they are connected. For simplicity, the power and Bluetooth connections are not shown. A filter can be added to improve signal to noise ratio.

FIG. 5 is a block diagram showing an example of how the electrical components of the surgical tool system are connected. A torque sensor, i.e., Wheatstone Bridge (strain gauges), take the measurements and the signal is amplified via an INA122. Optionally the signal from the torque sensor is filtered to reduce signal to noise ratio. The signals from the torque sensor is transmitted to the microcontroller, which is converted into digital signals via ADC. A rotational accelerometer, i.e., gyroscope, equipped with digital filters to reduce signal to noise ratio, is also transmitted to the microcontroller. The units for calculation of the energy measurements, generation of optimal ranges for the parameters and comparison between real time values and the optimal ranges are not shown. The microcontroller comprises a pulse width modulator ("PWM") and a pulse width modulator clock ("PWM CLK"), which process the signal corresponding to the results of the comparison to a vibration motor. The microcontroller may alternatively comprise a unit (Digital I/O) that process such signal and transmit to LED displays.

Figure 6:
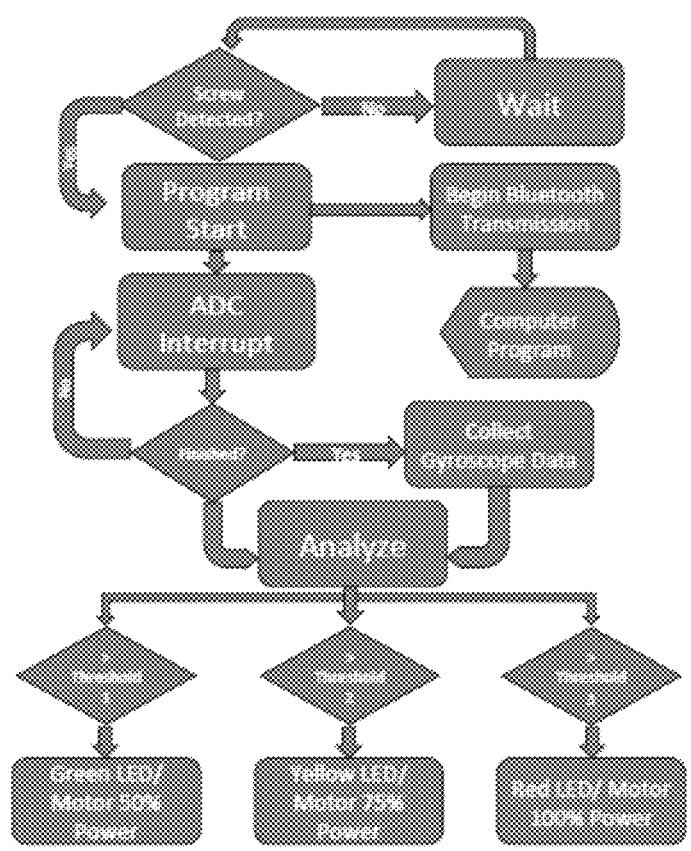
FIG. 6 is a flow chart of exemplary operations that carry out the embodiments of the present invention.

FIG. 6 is a flow chart showing one embodiment of how the surgical tool system is used to perform installation of a fixator. Processes depicted include detection of the start and end of the tapping or fixator operations as well as the sensor data acquisition and processing with comparison to thresholds stored in memory.

3. Methods a. Tapping

The present invention provides a method of installing a fixator in a biological tissue that minimize post-surgery loosening. In some embodiments, the insertion of the fixator is preceded by tapping. Tapping is a procedure a surgeon uses to drill a hole in the selected tissue to develop a trajectory of the fixator to be installed. Typically, the user identifies the location where the fixator is to be installed, and taps the location in the tissue using the surgical tool system disclosed herein. In some cases, a wire is laid along the trajectory to assist the insertion of the fixator. During the tapping process, torque measurements and rotational velocity measurements are taken at a high frequency in order to produce data in real time, i.e., at 5-60 Hz, or at least 5, 7, 10, 15, 20, 30 times per second for each, and values of at least one computed parameter derived from sensor data are calculated at each measurement and compared with one or more optimal ranges as described above.

b. Insertion of the Fixator

Next, the user chooses appropriate screw size based on the size of the tap used and the depth of the hole in the tissue. Typically, the size of the fixator, for example, a screw, is slightly larger in diameter than the diameter of the tap used to produce the hole in the tissue. Factors such as a person's age, gender, race, BMI, and BMD are considered in choosing the correct size, depth, and type of fixator. The user then loads the fixator onto the surgical tool to start to operate the tool and insert the fixator along the prepared trajectory. As in the tapping process, during the insertion process, torque measurements and rotational velocity measurements may be taken by two or more sensors with the surgical tool system of the invention, and at least one torque parameter and at least one energy parameter are calculated. In some embodiments, both the measurement and the calculations occur at a high frequency, e.g., at least 10, at least 12, at least 15, at least 20, or at least 30 times per second, or for example 5-60 Hz.

c. Feedback and Adjustment

In certain embodiments, the real time values of the at least one torque parameter and at least one energy-rotation parameter (and optionally one or more other derived parameters) may be compared with one or more optimal ranges. In some embodiments, the one or more optimal ranges are the optimal ranges for each individual parameters, as described above. In some embodiments, the one or more optimal ranges is one range for the property I, which is a composite value that takes into account of at least one torque parameter value and at least one energy-rotation parameter value and may contain one or more other derived parameters, as described above. If the real time values of these parameters fall outside the optimal ranges, the system may provide a feedback notifying the surgeon of such deviation. The feedback can be a visual feedback, i.e., providing a visual signal to the user, or a tactile feedback, i.e., providing a movement, e.g., a vibration, which can be sensed by the user. The user then can adjust the tapping or insertion operation, for example, adjusting the depth of the insertion and the torque exerted on the surgical tool until the feedback indicates that torque measurements and energy measurements are within the optimal ranges. In some embodiments, the user has the option to activate the feature in the surgical tool system, which automatically adjusts the insertion operation to maintain the torque and energy parameters within the optimal ranges.

EXAMPLE

The following Example has been included to provide guidance to one of ordinary skill in the art for practicing representative embodiments of the presently disclosed subject matter. In light of the present disclosure and the general concentration of skill in the art, those of skill can appreciate that the following Examples are intended to be exemplary only and that numerous changes, modifications, and alterations can be employed without departing from the scope of the presently disclosed subject matter.

Example 1

To accurately measure torque, a design consisting of four semiconductor strain gauges in a full Wheatstone bridge configuration was created. To maximize strain and produce a strong, clean signal from the strain gauges, a torque cell for mounting the strain gauges was designed using Solidworks 2015. Torque values previously recorded during surgical screw insertions were applied to the cell in a Solidworks FEA. The resulting strain values and properties of the strain gauges were used to determine the voltage output from the bridge circuit, which was amplified to an appropriate level (3V) for signal processing. NI Multisim 14.0 was used to simulate analog circuits and optimize their performance. To measure rotational velocity, which is needed to calculate energy, a three-axis gyroscope was chosen. The sensors were interfaced with a microcontroller, which performed 10-bit analog to digital conversion of the strain gauge signal, analyzed sensor data, and controlled LEDs and vibrating motors to provide feedback to clinicians. Circuit diagrams and printed circuit board (PCB) layouts were created using EAGLE 7.6. A single 3.6V battery was chosen to power the device. A Bluetooth module was also incorporated into the design to transfer data from the screwdriver to a computer for further analysis and performance tracking. FIG. 5 shows how the electronic components are interfaced together.

Simulated torque cell strains ranged from $30\times10'$ to $290\times10'$, which corresponded to a bridge output voltage of 12-115 mV. Amplifying the signal to 3V and converting it with a 10-bit analog to digital converter (ADC) resulted in a resolution of 2.9 mV. This resolution, and therefore torque measurement accuracy, could be improved by reducing the reference voltage of the ADC. At full power consumption with all devices and LEDs on, the battery life was calculated to be 10.4 hours for a 1.2 Ah battery; this should be sufficient to last an entire surgery because the device will rarely be used at full power. The PCB, sensors and battery all fit inside the screwdriver, making the device completely wireless.

This surgical screwdriver is designed to contain all necessary sensors, electronics, and processing components. It is capable of accurately measuring torque and rotational velocity and then providing real-time feedback to clinicians during surgery. The device will notify the surgeon when ideal insertional torque and energies are reached during screw insertion, and again if parameters move outside of optimal ranges, thus reducing the likelihood of screw loosening. Further prototyping and testing will be performed to optimize device performance.

What is claimed:

1. A method for installing a fixator in a biological tissue, the method comprising:
   a) loading a fixator to a surgical tool system,
   b) operating the surgical tool system to start installing the fixator in the biological tissue,
   c) receiving measurements from a first, second, and third sensors and calculating values of one or more torque parameters and one or more energy-rotation parameters,
   wherein said one or more torque parameters and one or more energy-rotation parameters comprise mean torque, mean rotational velocity, mean power, and total energy, based on the measurements,
   d) generating values of Property I, wherein each Property I value is a sum of weighted values of the one or more torque parameters and one or more energy-rotation parameters,
   e) generating a signal reflecting whether the Property I values fall outside one or more optimal ranges of Property I, and
   f) adjusting the operation of the tool such that values of Property I are within the one or more optimal ranges, if the values are outside the optimal ranges,
   g) repeating steps c)-f) until the installation is complete.

2. The method of claim 1, wherein the surgical tool system further comprises a power source.

3. The method of claim 1, wherein the second sensor comprises an accelerometer or a gyroscope.

4. The method of claim 1, wherein the first, second, and third sensors are configured to obtain measurements at a frequency of at least 5, at least 20, at least 40, or at least 60 Hz.

5. The method of claim 1, wherein one or more optimal ranges of Property I are generated based in part on one or more factors selected from age, gender, height, weight, body mass index, race, and bone mineral density.

6. The method of claim 1, wherein the the signal is a visual signal.

7. The method of claim 1, wherein the the signal is a tactile signal.

8. The method of claim 1, wherein the one or more torque parameters further comprise peak torque.

9. The method of claim 1, wherein the one or more energy-rotation parameters further comprise energy density.

10. The method of claim 1, wherein the fixator is a pedicle screw.

11. The method of claim 1, wherein the fixator is a cortical screw.

12. The method of claim 1, wherein the system further comprises a wireless transmitter module for data transmission and storage.

13. The method of claim 1, wherein the measurements are performed at a frequency of at least 10, at least 12, at least 15, at least 20, or at least 30 times per second.

14. The method of claim 1, wherein the signal is a visual signal or tactile signal.

15. The method of claim 1, wherein the fixator is a pedicle screw or a cortical screw.

16. The method of claim 1, wherein the method further comprises transmitting data from the tool via a wireless transmitter module.

17. A method for preparing for installing a fixator in a biological tissue, wherein the method comprises,
   i) tapping with a surgical tool in the location of the biological tissue where a fixator is to be installed,
   ii) receiving measurements from a first, second, and third sensors and calculating values of one or more torque parameters and one or more energy-rotation parameters, wherein said one or more torque parameters and one or more energy-rotation parameters comprise mean torque, mean rotational velocity, mean power, and total energy based on the measurements
   during the tapping,
   iii) generating a Property I value, wherein the Property I value is a sum of weighted values of the one or more torque parameters and one or more energy-rotation parameters, and
   iv) adjusting tap size if the Property I value falls outside optimal ranges of Property I, or
   continuing with tapping if the Property I value falls within the optimal ranges.

18. The method of claim 17, wherein the measurements are performed at a frequency of at least 10, at least 12, at least 15, at least 20, or at least 30 times per second.

* * * * *

UNITED STATES PATENT AND TRADEMARK OFFICE
CERTIFICATE OF CORRECTION

| | | |
|---|---|---|
| PATENT NO. | : 11,871,975 B2 | Page 1 of 1 |
| APPLICATION NO. | : 16/339400 | |
| DATED | : January 16, 2024 | |
| INVENTOR(S) | : Philip J. Brown, Andrea Morgan Rich and Aaron Ross Van Gorkom | |

It is certified that error appears in the above-identified patent and that said Letters Patent is hereby corrected as shown below:

In the Claims

Column 11, Claim 6, Line 42, "wherein the the signal" should read --wherein the signal--

Column 11, Claim 7, Line 44, "wherein the the signal" should read --wherein the signal--

Signed and Sealed this
Twenty-eighth Day of May, 2024

Katherine Kelly Vidal
*Director of the United States Patent and Trademark Office*